US009568339B2

(12) United States Patent
Abedin et al.

(10) Patent No.: US 9,568,339 B2
(45) Date of Patent: Feb. 14, 2017

(54) DBF FIBER LASER BEND SENSOR AND OPTICAL HETERODYNE MICROPHONE

(75) Inventors: Kazi S. Abedin, Basking Ridge, NJ (US); Paul S. Westbrook, Bridgewater, NJ (US)

(73) Assignee: OFS FITEL, LLC, Norcross, GA (US)

(*) Notice: Subject to any disclaimer, the term of this patent is extended or adjusted under 35 U.S.C. 154(b) by 491 days.

(21) Appl. No.: 13/990,617

(22) PCT Filed: Dec. 2, 2011

(86) PCT No.: PCT/US2011/063194
§ 371 (c)(1),
(2), (4) Date: Jun. 20, 2013

(87) PCT Pub. No.: WO2012/075474
PCT Pub. Date: Jun. 7, 2012

(65) Prior Publication Data
US 2014/0054451 A1    Feb. 27, 2014

Related U.S. Application Data

(60) Provisional application No. 61/419,247, filed on Dec. 2, 2010.

(51) Int. Cl.
| | | |
|---|---|---|
| G01D 5/26 | (2006.01) |
| G01J 1/04 | (2006.01) |
| G01L 11/02 | (2006.01) |
| G01H 9/00 | (2006.01) |
| G01L 1/24 | (2006.01) |
| G01N 21/77 | (2006.01) |

(Continued)

(52) U.S. Cl.
CPC .............. *G01D 5/268* (2013.01); *G01H 9/004* (2013.01); *G01J 1/0425* (2013.01); *G01L 1/243* (2013.01); *G01L 1/246* (2013.01); *G01L 11/025* (2013.01); *G01D 5/35316* (2013.01); *G01N 2021/7716* (2013.01); *H04R 23/008* (2013.01)

(58) Field of Classification Search
CPC .... G01L 11/025; G01L 11/242; G01L 11/243; G01L 11/245; G01L 11/246; G01L 11/247; G01H 9/004; G01J 1/0425; G01N 2021/7716; H04R 23/008; G01D 5/268; G01D 5/35316; G02B 6/34; G01S 3/067
See application file for complete search history.

(56) References Cited

U.S. PATENT DOCUMENTS 5,488,475 A * 1/1996 Friebele et al. .............. 356/478
5,513,913 A * 5/1996 Ball et al. ..................... 374/120
(Continued)

*Primary Examiner* — John Lee
(74) *Attorney, Agent, or Firm* — Sam S. Han, Esq.

(57) ABSTRACT

Methods and systems using one or more distributed feedback (DFB) lasers for capturing changes in the lasing environment are disclosed. Specifically, a sensor for measuring a measurand, such as pressure or temperature, or changes in a measurand, includes a fiber with at least one core, at least one fiber laser cavity formed by a single fiber grating in the core, wherein the laser operates on at least two modes along at least part of its length. The DFB laser includes a section that is bent into a non-linear shape and at least one pump laser connected to the fiber laser cavity. When the DFB laser experiences a perturbation or measurand change that changes the spacing of the modes, a change in an RF beat note is generated. This beat note can then be measured and related to the measurand change.

20 Claims, 11 Drawing Sheets

(51) Int. Cl.
*H04R 23/00* (2006.01)
*G01D 5/353* (2006.01)

(56) References Cited

U.S. PATENT DOCUMENTS

| | | | |
|---|---|---|---|
| 5,564,832 A * | 10/1996 | Ball et al. | 374/161 |
| 5,696,579 A * | 12/1997 | Johnson | 356/35.5 |
| 5,818,982 A * | 10/1998 | Voss et al. | 385/13 |
| 5,844,927 A * | 12/1998 | Kringlebotn | 372/6 |
| 6,055,080 A * | 4/2000 | Furstenau et al. | 398/139 |
| 6,597,821 B1 * | 7/2003 | Bohnert et al. | 385/12 |
| 6,630,658 B1 * | 10/2003 | Bohnert et al. | 250/227.14 |
| 6,668,105 B2 * | 12/2003 | Chen et al. | 385/13 |
| 6,668,656 B2 * | 12/2003 | Fernald et al. | 73/705 |
| 6,865,194 B1 * | 3/2005 | Wright et al. | 372/6 |
| 6,885,784 B2 * | 4/2005 | Bohnert | 385/12 |
| 6,901,187 B2 * | 5/2005 | Haroud et al. | 385/37 |
| 7,062,973 B2 * | 6/2006 | Tam et al. | 73/705 |
| 7,120,340 B2 * | 10/2006 | Berkey et al. | 385/123 |
| 7,251,023 B2 * | 7/2007 | Bohnert et al. | 356/73.1 |
| 7,518,730 B2 * | 4/2009 | Yates et al. | 356/480 |
| 8,290,316 B2 * | 10/2012 | Molin et al. | 385/12 |
| 8,451,453 B2 * | 5/2013 | Molin et al. | 356/480 |
| 2002/0041724 A1 * | 4/2002 | Ronnekleiv et al. | 385/12 |
| 2002/0117608 A1 * | 8/2002 | Ogura | 250/227.14 |
| 2002/0154291 A1 * | 10/2002 | Uchiyama et al. | 356/73.1 |
| 2002/0194917 A1 * | 12/2002 | Fernald et al. | 73/705 |
| 2004/0071400 A1 * | 4/2004 | Haroud et al. | 385/37 |
| 2004/0083808 A1 * | 5/2004 | Rambow et al. | 73/250 |
| 2004/0093950 A1 * | 5/2004 | Bohnert | 73/705 |
| 2004/0197050 A1 * | 10/2004 | Lovseth et al. | 385/37 |
| 2004/0245444 A1 * | 12/2004 | MacDougall | 250/231.19 |
| 2006/0013534 A1 * | 1/2006 | Bohnert et al. | 385/37 |
| 2006/0070446 A1 * | 4/2006 | Tam et al. | 73/705 |
| 2006/0126435 A1 * | 6/2006 | Tam et al. | 367/149 |
| 2006/0146337 A1 * | 7/2006 | Hartog | 356/478 |
| 2008/0085074 A1 * | 4/2008 | Wakahara et al. | 385/13 |
| 2009/0126501 A1 * | 5/2009 | Ferguson | 73/800 |
| 2009/0129722 A1 * | 5/2009 | Hao et al. | 385/13 |
| 2009/0195785 A1 * | 8/2009 | Blin et al. | 356/460 |
| 2010/0220332 A1 * | 9/2010 | Digonnet | 356/465 |
| 2011/0019179 A1 * | 1/2011 | Molin et al. | 356/32 |
| 2011/0122417 A1 * | 5/2011 | Molin et al. | 356/478 |
| 2011/0311179 A1 * | 12/2011 | Greenaway | 385/12 |
| 2014/0054451 A1 * | 2/2014 | Abedin et al. | 250/227.14 |
| 2014/0112357 A1 * | 4/2014 | Abedin et al. | 372/3 |
| 2014/0269789 A1 * | 9/2014 | Westbrook et al. | 372/6 |

* cited by examiner indicates direction of slow axis indicates direction of slow axis

DBF FIBER LASER BEND SENSOR AND OPTICAL HETERODYNE MICROPHONE

CROSS REFERENCE TO RELATED APPLICATIONS

The present application claims the benefit of U.S. Provisional Patent Application Ser. No. 61/419,247 filed on Dec. 2, 2010, which is incorporated herein by reference in its entirety.

BACKGROUND

Optical fiber Bragg gratings are commonly used as sensors of measurands, such as pressure and temperature. Such sensors typically employ a mechanical arrangement that couples an external pressure to compressive or tensile strain of the optical fiber. Thus, a Bragg wavelength of the grating can be related to the external pressure. In order to remove temperature dependence, a second grating with no strain is typically included as well. This second grating is sensitive to temperature but not to strain. A deconvolution of the two grating wavelengths then results in the measurements of pressure and temperature. Another known way of sensing of temperature, pressure, stress and similar other external perturbations is by the use of a single frequency fiber laser. A single frequency fiber laser can be made of a small gain fiber and a pair of Bragg gratings that act as distributed Bragg reflectors (DBR), or a phase-shifted distributed feedback (DFB) laser inscribed on the gain fiber. Since the external perturbations can cause a change in the laser oscillation frequency through the use of suitable mechanical transducer attached to the laser, by measuring the change in wavelength accurately, one can measure the extent of this external perturbation.

Such sensors have two defects that hamper performance. First, they require high performance bonding and mechanical fixtures so that the fiber may be placed under tension in a reliable fashion. Second, they require optical sources and wavelength sensitive readout modules to obtain the pressure and temperature data.

A second deficiency of the prior art is that wavelength-dependent detectors and/or sources are required to extract the measurand. In cases where high sensitivity is desired, either the detector must have high precision or the source must have narrow linewidth. Such sources and detectors are expensive and difficult to maintain in harsh environments. Other drawbacks include a means for coupling various measurands, such as pressure, to the bending of a fiber, a means for sensing bends in the fiber in a robust manner with one grating and RF detection, and a means to measure very small fiber bends such as those arising from acoustic variations.

Accordingly, new and improved sensing methods and apparatuses that overcome the above limitations of the prior art are required.

SUMMARY OF THE INVENTION

In accordance with an aspect of the present invention, a sensor to sense a measurand is provided. Specifically, a sensor for measuring a measurand or a change in a measurand, such as temperature or pressure, includes a fiber with at least one core, at least one fiber laser cavity formed by a single fiber grating in the core, wherein the laser operates on at least two modes along at least part of its length. The DFB laser includes a section that is bent into a non-linear shape and at least one pump laser connected to the fiber laser cavity. When the DFB laser experiences a perturbation or measurand change that changes the spacing of the modes, a change in an RF beat note is generated. This beat note can then be measured and related to the measurand change.

The sensor may further include a structure connected to the fiber that converts a change in the measurand into a change of the non-linear shape of the first section of the fiber laser cavity. In accordance with an aspect of the invention, a change in the measurand causes a shift in the modes of the fiber laser cavity, thereby causing the RF beat note to change. The sensor may further comprise a RF detector connected to the fiber laser cavity that detects the generated RF beat note. The single fiber grating can be a distributed feedback laser.

In accordance with further aspects of the invention, the fiber laser cavity has a fiber cross-section with anisotropic pressure properties that cause radially asymmetric strain of the fiber, thereby causing the fiber to bend as a result of changing measurands, such as pressure or acoustic vibration. The properties can be imparted by one or more coatings applied to the fiber or suitable holey structures in the fiber.

The sensor can also include an optical detector connected to the distributed feedback fiber laser. Further, the sensor can also include a frequency demodulator connected to the optical detector. In accordance with one embodiment of the present invention, the fiber laser cavity has a slow axis and a fast axis of birefringence along at least part of its length. The measurand can be a pressure or a temperature or a vibration or a chemical reaction. In accordance with a further embodiment of the present invention, the sensor is part of an optical heterodyne microphone.

Corresponding methods are also contemplated. In accordance with one of the methods, the fiber laser cavity is excited with a pump laser. The method includes exposing the sensor to a perturbation, the sensor comprising a fiber with at least one core, at least one fiber laser cavity formed by a single fiber grating in at least one core, the fiber core comprising the fiber laser cavity having at least two modes propagating along at least part of its length, the at least one fiber cavity including a first section that is bent in a non-linear shape and at least one pump laser connected to the fiber laser cavity. The perturbation can be applied to a structure connected to the sensor. The method can also include detecting a RF beat note generated by the perturbation with a RF detector connected to the fiber laser cavity.

In the method, the fiber laser cavity can have a fiber cross-section with anisotropic pressure properties that cause radially asymmetric strain of the fiber, thereby causing the fiber to bend as a result of changing pressure or vibrations. Also, the fiber laser cavity can have a slow axis and a fast axis of birefringence along at least part of its length.

In accordance with another embodiment of the present invention, a sensor can include at least a single fiber having more than one core, for example, two cores, with a distributed feedback laser in each core. The distributed feedback lasers are subject to a perturbation, wherein the cores may operate on multiple modes such that each mode has a propagation constant, there by each DFBs generating their own beat note and the perturbation causes a shift in the propagation constants thereby causing the RF beat notes of each DFB made in cores to change. (Note that beat noise exists even in the absence of any perturbations). The sensor can also include a RF detector connected to the distributed feedback lasers that detects the generated RF beat note. In accordance with further aspects of the present invention, multiple distributed feedback lasers are provided. In accordance with yet another embodiment, the distributed feedback lasers each operate on a single mode, and differences in propagation constants of the lasers results in a beat frequency which may be detected by a detector.

DESCRIPTION OF PREFERRED EMBODIMENTS

Figure 1:
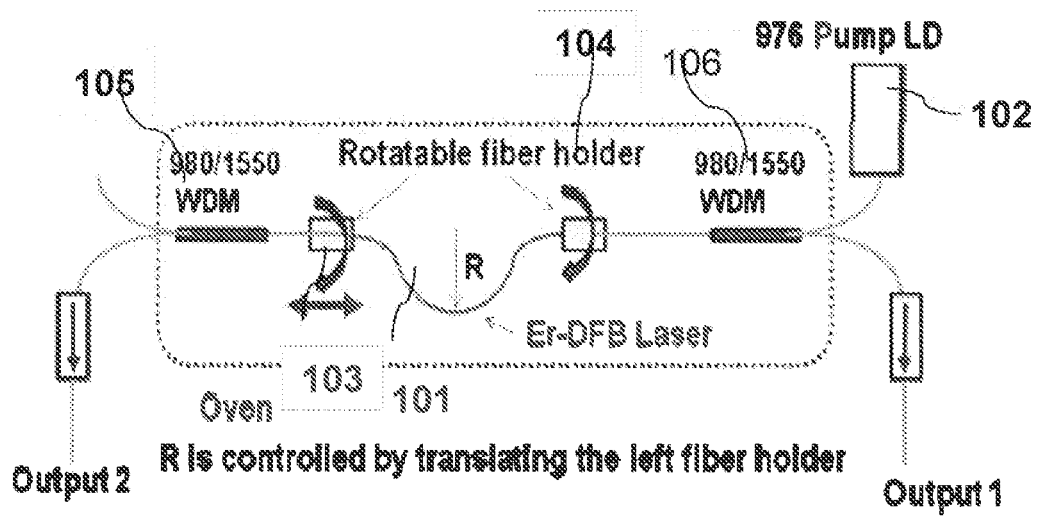
FIG. 1 illustrates an experimental set-up in accordance with an aspect of the present invention.

A fiber laser comprises, among other things, a fiber laser cavity and a pump source or pump laser that causes the fiber laser cavity to lase. One example of a fiber laser cavity is a distributed feedback laser ("DFB") cavity. In this case, the fiber laser cavity may be formed by a single fiber Bragg grating inscribed in the core of the fiber. Other examples of fiber laser cavities include distributed Bragg reflector (DBR) cavities, ring cavities, and cavities formed by bulk optics mirrors coupled to a fiber.

One aspect of the present invention is to use a waveguide laser such as a DFB fiber laser or a DFB planar waveguide laser subject to induced birefringence along at least part of the cavity forming the laser for measuring pressure and temperature. Generally speaking, the DFB laser has a section of periodic grating with a discrete phase shift (nominally $\pi$) in the intermediate region, typically offset form the center by a few percent of the length of the grating. This grating can be inscribed by appropriate UV exposure on the fiber DFB laser, and by lithographic technique in the case of DFB planner waveguide laser. The region of the grating is doped with suitable gain medium such as a rare earth element, such as erbium, ytterbium, erbium/ytterbium, thulium, and thus could provide optical amplification (gain), when energized using pump source with wavelength that is appropriate for the gain medium. Laser output can be extracted in the forward direction (in the direction of pump wave propagation) or in the backward direction using an optical circulator or suitable wavelength division multiplexer (WDM) coupler. When the direction of offset in phase shift is away from the pump, the output is primarily obtained in the forward direction, and vice versa. In one embodiment of the present invention this can be configured as a DFB fiber laser that is bent. Bending the DFB fiber induces birefringence, which is a measure of the difference in propagation constant between two polarization modes of the propagating light. This induced birefringence changes the lasing characteristics of the laser and can be related to many measurands, including pressure, displacement and acoustical disturbances, or any perturbation with alters the birefringence or the propagation constants of the modes supported by the DFB fiber.

According to an embodiment of the present invention, the lasing frequency is related to the measurand. According to another embodiment of the present invention, the laser operates on at least two modes, which may be two polarization modes, at least one of which is sensitive to the measurand. In a more general sense, any perturbation to the fiber or waveguide that changes the propagation constants of the lasing modes (spatial or polarization) will alter the lasing characteristics of the laser. A DFB fiber having a core, sufficiently large to support the fundamental mode, $LP_{01}$, and one or more higher order modes, such as $LP_{11}$, $LP_{02}$, $LP_{21}$, and the like, can be operated on the fundamental mode and one or more of these higher order modes. Since the effective indices (equivalently the propagation constants) are different for these spatial modes, their lasing wavelengths will be non-degenerate. Differences in propagation constants of at least two modes results in a beat frequency between those modes and can be related to the measurand, which is configured to be influenced by the bent or perturbed state of the cavity. According to yet another embodiment of the present invention, the measurand is related to both optical and beat frequency measurements.

Intensity modulation or beating can occur when two coherent light waves with different optical frequencies (i.e. wavelengths) are combined. Such phenomena can be detected with a photodetector. Consequently, beating can be caused by two polarization modes (with suitable polarizer or applying polarization dependent loss (PDL)) of a single laser cavity such as a DFB laser with non-zero birefringence. Similarly, beating also can be produced between the various fiber modes that may oscillate in a single DFB cavity configured for such oscillation. Beating can also be observed between the output of lasers that are spatially or physically isolated, such as DFB or DBR lasers formed using dual-core, or two (or more) multicore fibers.

Beat frequency $\Delta v$ can be expressed as $\Delta v = cB/(n\lambda)$, where c is the velocity of the propagating light, B is the difference between effective indices of two oscillating modes in the light, n is a nominal effective index, and $\lambda$ is the average wavelength of the two modes. Depending on the index profile, shapes of core/cladding, and distance of the core from the physical axis of the fiber, the birefringence and its influence by external perturbations (such as bending, stress, temperature change) can vary by a large amount. For example, the index difference between the polarization modes can be as low as $\sim 10^{-5}$ (residual birefringence in non-pm fibers) and as high as $10^{-3}$ for higher-order modes in a step index-type few mode fiber. This would result in a beat frequency in the range of few hundred MHz to 100 GHz or even more. For convenience of RF detection, one would prefer a beat frequency not exceeding 100 GHz. For higher frequencies, one would find it easier to use an optical method using an optical spectrum analyzer or incorporating a Fabry-Perot interferometer to measure the wavelengths of lasing components. One can also employ a fiber with a step index core having a parabolic profile, surrounded by a high index annular ring or similar feature that provides the right balance of effective index mismatch while maintaining the magnitude of perturbation for RF beat note in a range that is convenient for the user to measure.

According to yet another embodiment of the present invention, the DFB fiber laser is twisted, and the degree of twist is determined from the beat note, which in yet another embodiment of the present invention, is a radio frequency (RF) signal. According to yet another embodiment of the present invention, the DFB fiber is subjected to lateral stress. This may be accomplished by placing the DFB fiber between two plates. When the plates are pushed together, the related birefringence will change, thus changing the beat note frequency.

In yet another embodiment of the present invention, the pump of a DFB fiber laser is modulated in time. If more than one DFB laser is in the link, then the beat notes from each laser will occur within different time slots. Thus, even if the beat notes have similar frequencies, a time domain analysis of the propagating signals can be used to separate the beat signals from the different lasers. In yet another embodiment of the present invention, the optical fiber has more than one core with more than one core comprising a laser cavity. As the fiber is bent or twisted, subjected to acoustic vibrations, longitudinal or lateral stress, external pressure, or otherwise perturbed, each cavity will produce light at a different frequency, dependent on the state of perturbation.

A bend sensor is a sensor that is suited or configured for measuring the amount of bending. In a preferred embodiment of the present invention, a bend sensor comprises a fiber DFB laser operating on two polarizations while in another embodiment of the present invention, the laser operates on multiple spatial modes such as transverse modes or multiple longitudinal modes. In such instances, slight differences in the propagation constants of the modes will create the beat note. The DFB laser is energized by a pump radiation supplied by a remote pump source. Operation on two polarizations produces a beat note at an optical detector in a readout module. This beat note can be related to a state of bend or twist of the DFB cavity, or any other perturbation which may alter the birefringence of the laser cavity. Alternately, or in addition to, a bend or twist of a fiber, the fiber may be strained across its cross-section asymmetrically, and in yet another embodiment of the present invention, such a strained fiber has a non-circular or asymmetric shape that causes the measurand field to induce birefringence in the cavity.

In order to measure temperature, another embodiment of the present invention includes a second DFB cavity in the sensor. The beat note or response from this second laser can be configure to remain free from the influence of external perturbations (e.g. without affixing to any transducer) and thus becomes sensitive primarily to ambient temperature. While beat notes can be used for the measurements, it is also possible to use the optical wavelength to determine the temperature in the surrounding environment.

In yet another embodiment of the present invention, the fiber will be restricted to bend in a certain plane that will ensure a fixed angle of inclination of the birefringence axes with respect to the bending plane. When the plane of the bend sensor is along either of the birefringence axes (slow or fast), the beat frequency change becomes maximum, However, when the plane of the bend sensor is oriented at 45 degree with respect to the birefringence axes, beat frequency change will nominally be zero.

EXPERIMENTAL SETUP

Figure 2:
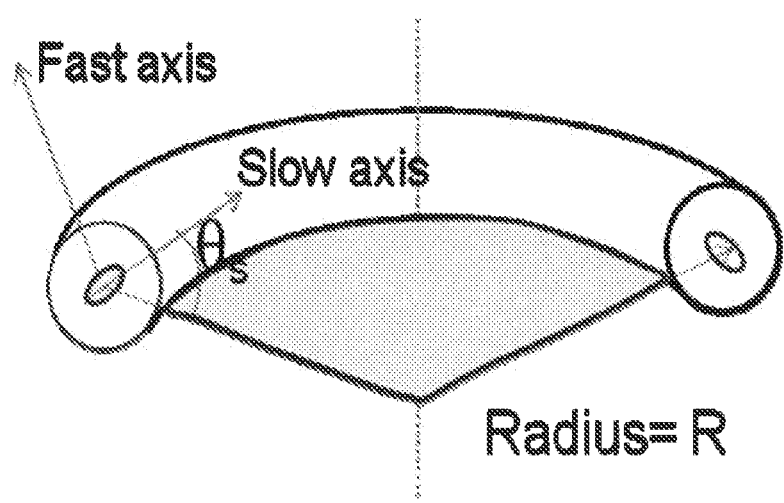
FIG. 2 illustrates a fiber with a fast axis and a slow axis of polarization birefringence, and shows the orientation of these axes with respect to a bend of the fiber, r.

Experiments were performed using an experimental setup shown in FIG. 1. Here, an Er doped distributed feedback (DFB) fiber laser 101, pumped at 976 nm with a pump laser 102 was used as a bend sensor. Any gain media can be used, such as fiber doped with Yb, Nd, Tm, Cr or the like. The DFB laser was held using two rotatable fiber holders 103 and 104, the spacing between which could be adjusted by using a mechanical translation state. Furthermore, two wavelength division multiplexers (WDMs) 105 and 106 were used as couplers to separate the output signals from the pump signal. The DFB laser was bent simply by moving the fiber holders closer using the translation stage. This setup also allowed 1) to remove any twist in the DFB laser or 2) to intentionally apply twist by rotating one holder relative to the other one. Further, by restricting the plane of bend of an un-twisted DFB laser to a certain orientation (e.g. horizontal plane) using a narrow planar guide (not shown in the FIG. 1), the angle of inclination $\theta_s$ of the polarization axis (slow or fast) was varied with respect to the bend plane. The orientation of the orthogonal birefringence axes of the fiber with respect to the bend plane is illustrated in FIG. 2.

The temperature of the DFB sensor was varied over a range of 25°-50° C. using an electrically controlled oven. The laser outputs (about 90% from one end and 10% from the other end, due to offset in the location of the discrete phase shift with respect to midpoint) were used to measure the lasing wavelength by monitoring with a wavelength meter and the RF beat note using a photodiode and RF spectrum analyzer.

Figure 3:
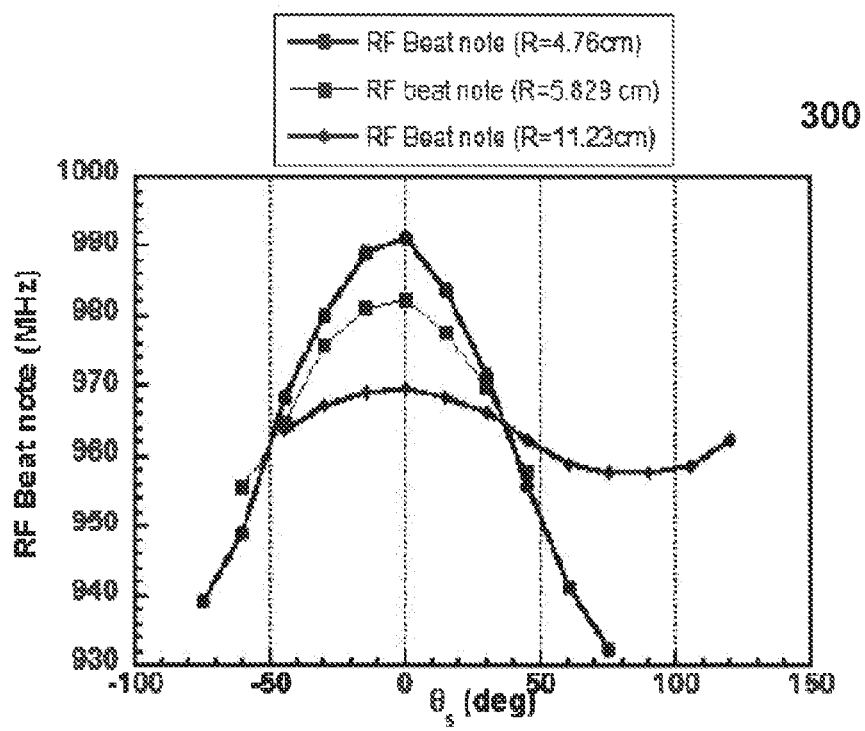
FIGS. 3-8 each provide a graph that illustrates properties of a DFB Fiber Laser Bend Sensor in accordance with an aspect of the present invention.
Figure 4:
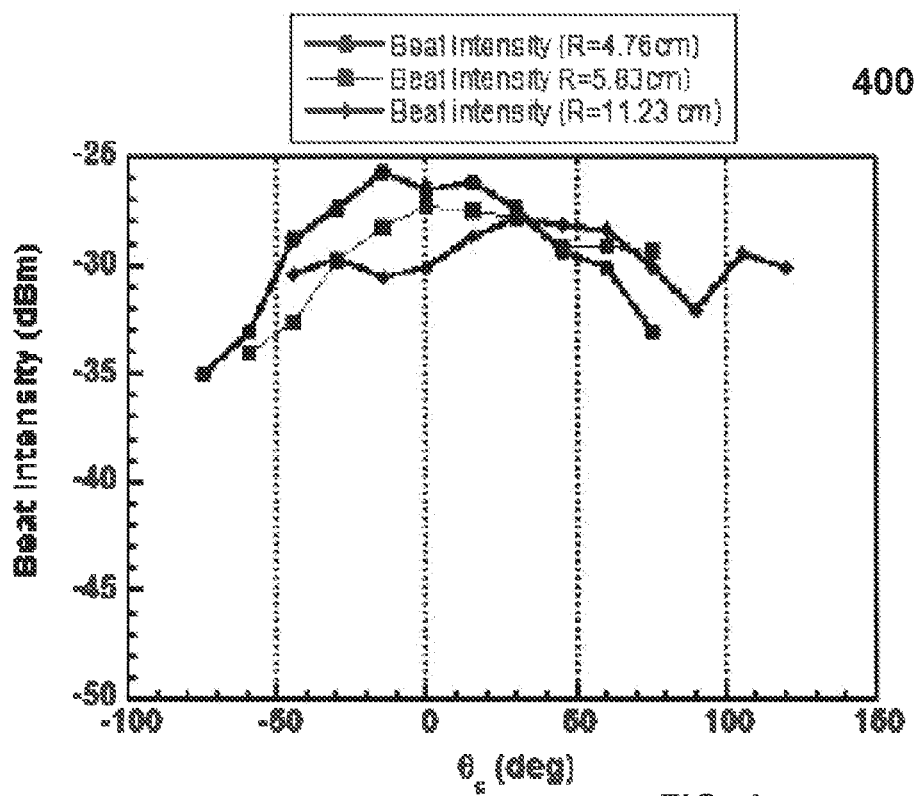

FIGS. 3 and 4 are graphs 300 and 400 illustrating the RF beat note measured under different inclination angle $\theta_s$ and different amount of bending (R: radius of curvature of bend shown in FIG. 1). The laser without a twist was readily oscillating with dual polarizations, yielding an output power of about 2.4 mW at 1545 nm. The beat frequency $\Delta v$ of the DFB laser when configured in a straight, unbent position was measured to be 964 MHz at room temperature. Using $\Delta v = cB_o/(n\lambda)$, an internal birefringence $B_o$ of the fiber was estimated at about $7.25 \times 10^{-6}$. $B_o$ may be approximated by the difference between the effective indices of the two polarization modes at the average wavelength of the two modes: $B_o = n_{slow} - n_{fast}$.

Figure 5:
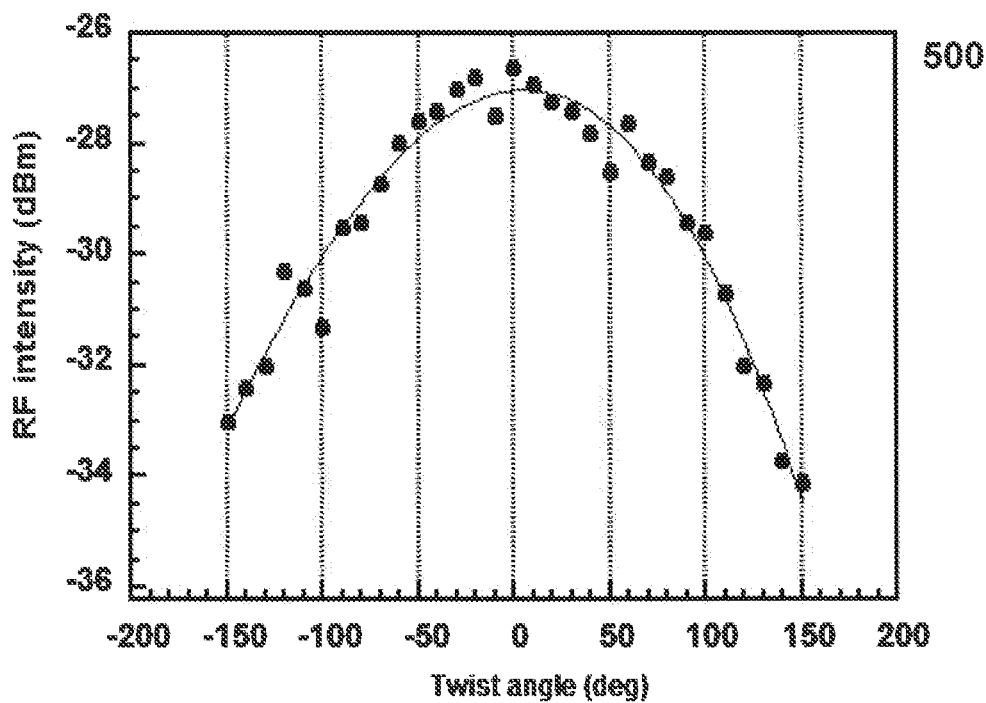

It is clearly seen that both the RF beat note and the beat intensity maximize at $\theta_s = 0$, which corresponds to the slow axis lying on the bend plane. Furthermore, the RF beat note increases as radius of curvature of bend decreases (for tighter bend). To obtain a strongest beat signal, it is also important to keep the DFB laser free from any twist in the axial direction (as shown in graph 500 in FIG. 5). The benefit of maintaining the DFB free from twist is that the birefringence change due to bending in different parts of the DFB becomes additive, and thus gives maximum beat frequency change due to bending.

Figure 6:
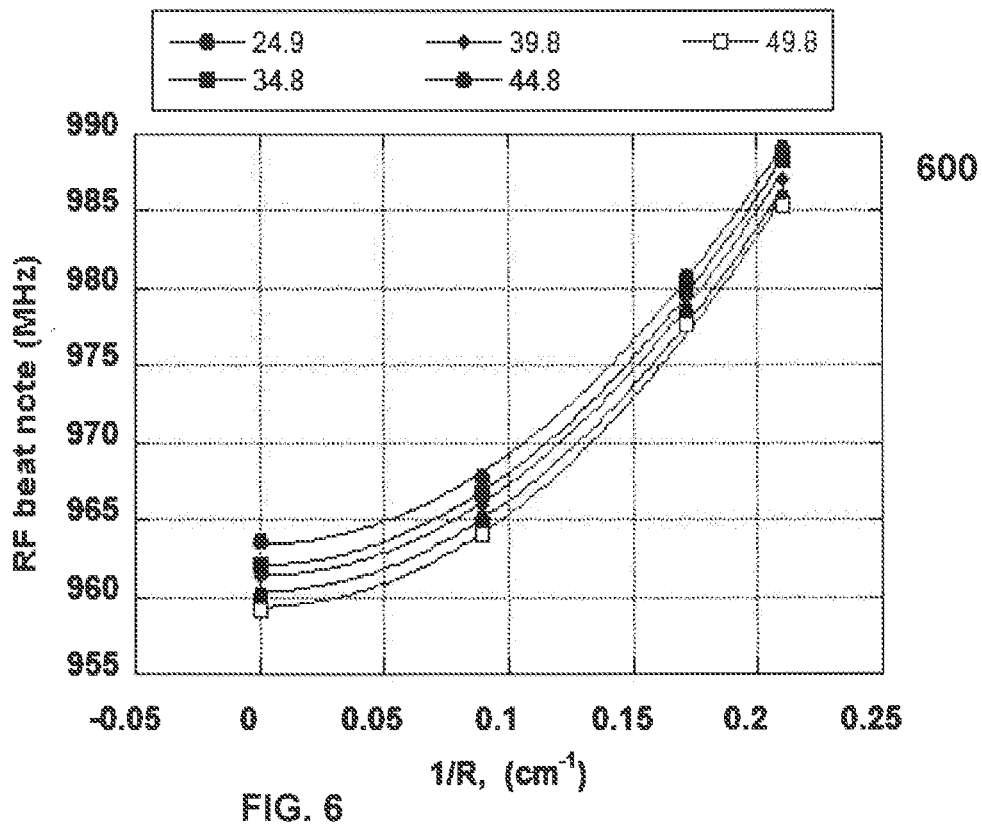

FIG. 6 in graph 600 shows the measured RF beat notes in 'frequency' versus '1/R' curves at five different temperatures. Here, the slow axis was lying in the plane of the bend, ensuring a largest shift in the RF beat note when the fiber is bent. In one embodiment of the present invention, the beat note vs. '1/R' curves are well fit with parabolic curves, expressed as $\Delta v = C_1 + C_2 (1/R)^2$. Here, $C_1$ and $C_2$ are two constants that depend on the temperature, birefringence of the fiber, cladding radius, bend radius, wavelength, mechanical and opto-mechanical properties of the fiber.

The following table provides a value for the coefficients C1 and C2 as a function of a temperature of the fiber DFB laser. These parameters can take different values, as the properties of the gain fiber changes.

| Temperature, ° C. | $C_1$, MHz | $C_2$, MHz*cm$^2$ |
|---|---|---|
| 29.8 | 963.44 | 583.94 |

-continued

| Temperature, °C. | $C_1$, MHz | $C_2$, MHz*cm² |
|---|---|---|
| 34.8 | 962.10 | 595.10 |
| 39.8 | 961.41 | 591.02 |
| 44.8 | 960.38 | 589.66 |
| 49.8 | 959.39 | 599.65 |

Figure 7:
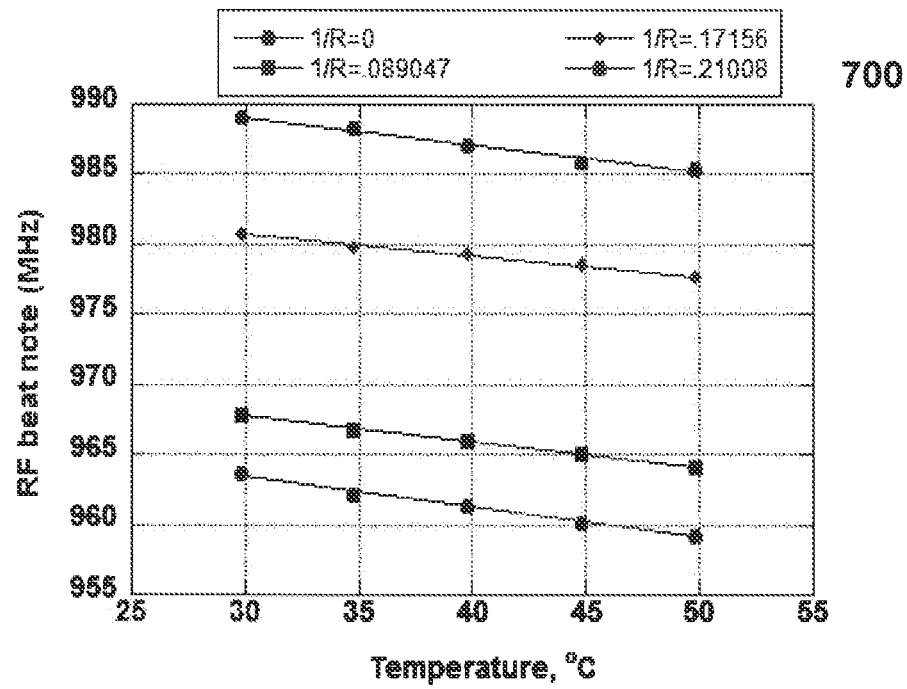

FIG. 7 in graph 700 plots the RF beat note at different operating temperatures under four different bending conditions. A linear dependence of beat note on the temperature can be readily seen.

Figure 8:
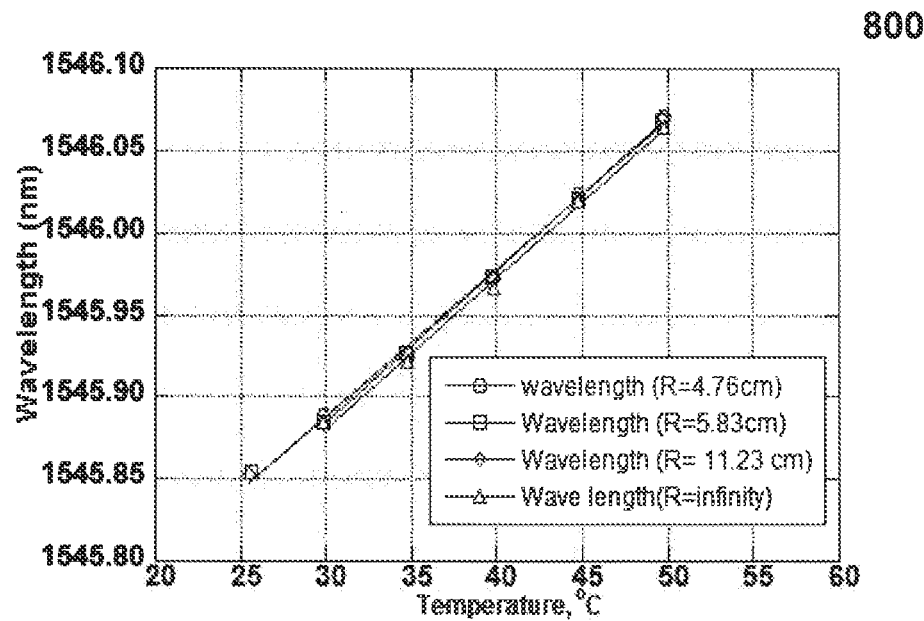

FIG. 8 in graph 800 shows the variation of wavelength with temperature under 4 different bend conditions. While wavelength is seen to vary on temperature, it is almost independent of the bend radius.

From these experimental results a matrix of coefficients can be derived to relate the beat note change $\delta(\Delta v)$, wavelength change ($\delta\lambda$) with the two measurands temperature change $\Delta T$ and change in bend radius change in the following way, $$\begin{vmatrix} \delta(\Delta v) \\ \delta\lambda \end{vmatrix} = \begin{vmatrix} k_{11} & k_{12} \\ k_{21} & k_{22} \end{vmatrix} \cdot \begin{vmatrix} \delta(1/R^2) \\ \delta T \end{vmatrix}, \text{ where}$$

$$\begin{vmatrix} k_{11} & k_{12} \\ k_{21} & k_{22} \end{vmatrix} = \begin{vmatrix} 591.4(\text{Mhz}*\text{cm}^2) & 0.186(\text{MHz}/°\text{C.}) \\ 0 & 9.11(pm/°\text{C.}) \end{vmatrix}.$$

The wavelength and the RF beat note can also be related to the temperature and the bend radius by the following equations, $$\Delta v = 969.8 - 0.214T + 591.4*(1/R)^2$$

$$\lambda = 1545.6 + 9.11*10^{-3}T.$$

These equations also allow the determination of the temperature T and bend radius R by measuring $\delta v$ and $\lambda$.

It is also possible to determine R and T from only RF measurements if there are two DFB lasers with one laser being held either straight or in a constant bend position. In one embodiment of the present invention a DFB fiber laser bend sensor and a reference DFB laser are provided. In another embodiment of the present invention, the reference DFB laser is a straight DFB laser and the second DFB laser is subjected to bending. The beat note from this reference can be configured to remain free from external perturbations (e.g. with out affixing to any transducer) and thus becomes sensitive primarily to ambient temperature. The beat notes of the second laser and the reference lasers can be expressed by $\Delta v_1 = C_{01} + C_{02} \cdot T + C_{03}/R^2$ and $\Delta v_2 = C_{01} + C_{02} \cdot T$, respectively. From $\Delta v_1$ and $\Delta v_2$, the measurands T and R can be determined. In these equations it is assumed that the pressure causes the DFB laser to bend in a perfectly circular form. When there is a deviation from the perfectly circular shape, a polynomial expression can be used to express or to approximate the dependence of $\delta v$ and R. In one embodiment of the present invention, $\Delta v$ is expressed or approximated by $C_{01} + C_{02} \cdot T + C_{03}/R^2 + C_{04}R + C_{05}/R^3$ depending on the anticipated shape of the bend. For a given transducer exposed to a given environment, the fiber of the laser may deform in a definite form and this coefficient can, in this case, be pre-calibrated. In another embodiment of the present invention, a lookup table is used that will relate $\Delta v$ as a function of R and T, i.e., $\Delta v = f(R,T)$.

In order to measure the pressure of a surrounding medium, the fiber DFB laser may be connected to a transducer whose displacement is proportional to pressure. In general, this displacement would be related to a variable bend of the DFB laser.

Figure 9A:
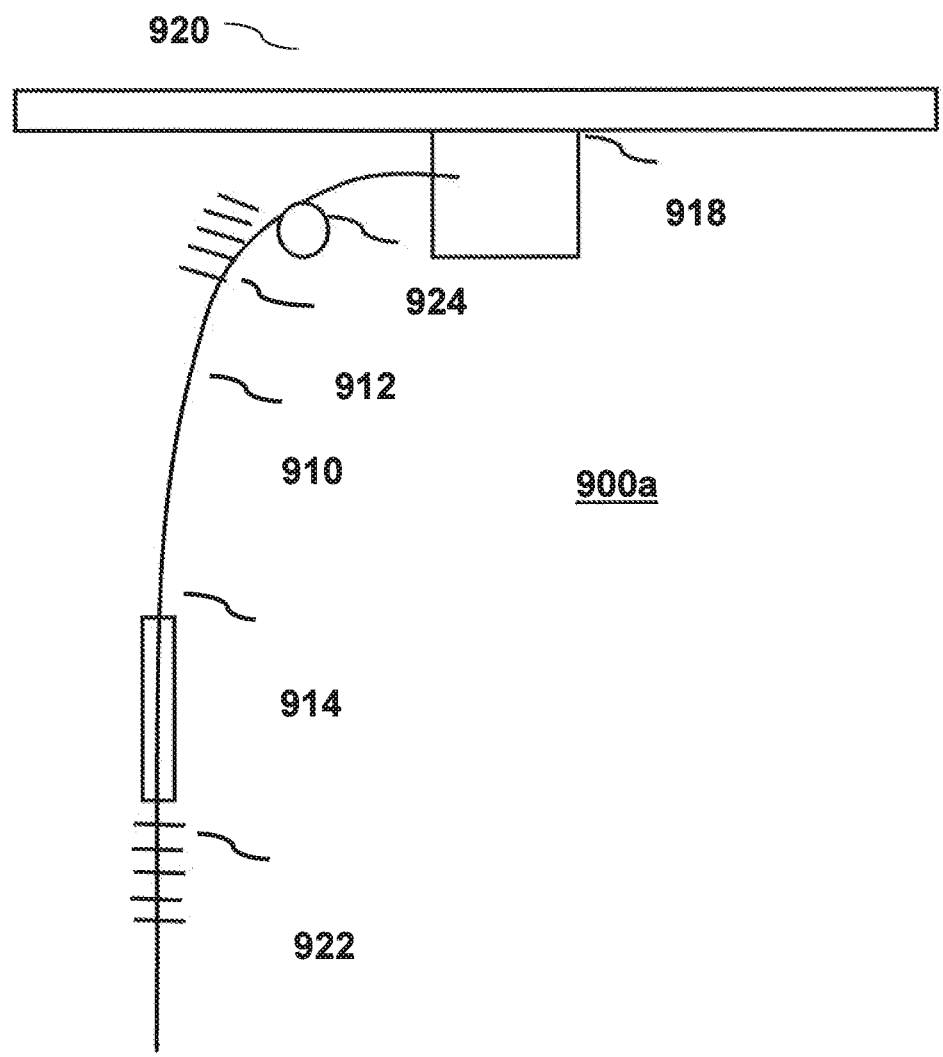
FIGS. 9a and 9b illustrate a transducer in accordance with an aspect of the present invention.

One such transducer is illustrated in FIG. 9a. Transducer 900a contains a DFB fiber 910 with at least one grating 912. The transducer has a moveable holder 918 which holds an end of fiber 910. The holder 918 is moveably attached to a rail or guide 920. The holder 918 moves along guide 920 as a consequence of a physical change. Such a physical change may be a change in temperature, pressure, acceleration or any other physical effect that can be converted into a displacement. Fiber 910 is guided through a guide 914, such as an open tube, which is stationary in the transducer. By moving holder 918, grating 912 experiences a change in bending. To facilitate this bending, the fiber 910 may be positioned hanging over a support or pulley 924. When holder 918 is positioned to the left of guide 920, the grating 912 may be almost straight, thus not experiencing any significant bending. The movement of the holder 918 is restricted between a position that is just above the pulley 924 and further to the right to a point, which causes the 912 sits on the pulley. As holder 918 moves to the right due to a changing physical effect or perturbation, fiber 912 is forced into a bent position, increasing as holder 918 moves further to the right along guide 920. This bending effect can be measured, for example, using the beat signal as described above. Further, fiber 910 may also be provided with a straight grating 922, which may be used to correct for temperature effects on the fiber. Other structural arrangements which convert the translation of one part of the structure into a change in bend radius of the DFB fiber laser fall within the scope of the invention.

Figure 9B:
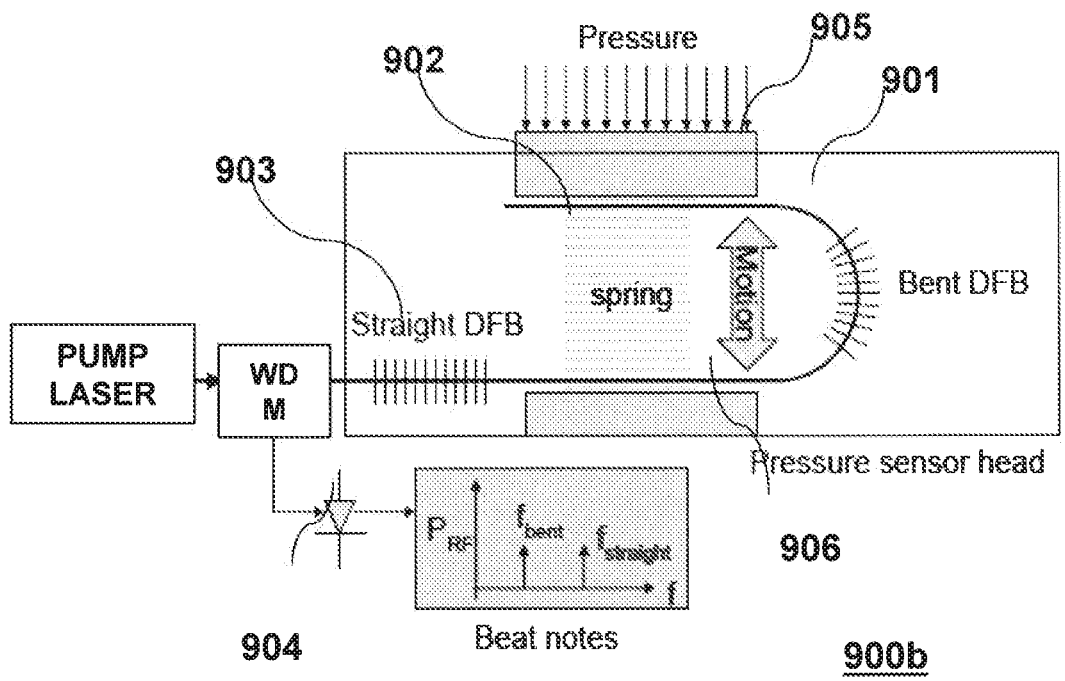

Another embodiment of a fiber transducer for measuring pressure is shown in FIG. 9b. In this illustrative embodiment, an apparatus 900b is provided that incorporates bending of a DFB fiber laser in response to a pressure applied to the apparatus. As shown in FIG. 9b, a DFB fiber laser 901 is positioned between a fiber holder 905 and a fiber holder 906. The fiber holders 905, 906, which may be plates, for example, may keep at least one or more linear parts of the fiber laser 901 in place, according to an aspect of this embodiment. In an alternate configuration, the fiber laser 901 is allowed to slide freely along at least one or both holders 905, 906, without being twisted. Twisting can change how bending influences the birefringence on the DFB laser, and thus can affect measurement accuracy. So, in this case, it is preferred to avoid any spurious twist.

In one embodiment, holder 905 is a pressure plate or membrane that moves due to an increase or decrease in external pressure experienced by apparatus 900b, such as, for example, an acoustic signal. In FIG. 9b, this pressure causes a displacement of holder 905 diaphragm against a mechanical spring 902. Such pressure causes a displacement of the spring and a change in the bending radius of fiber DFB laser 901. The spring 902 functions as a bias device that forces the holder 905 and the fiber laser 901 to a precalibrated neutral position. The displacement of the spring 902 and of holder 905 is then coupled to the change in bend of the DFB laser 901. When an increase in pressure occurs, holders 905 and 906 move closer together, compressing spring 902, and decreasing the bend radius of laser 901, thereby changing the related birefringence and the beat note, which is then utilized to capture the change in pressure. Note that many other spring or bias arrangements are possible and configuration 900b of FIG. 9b is only an illustrative example. Other spring arrangements and bias configurations are possible and are fully contemplated to fall within the scope of the invention. For instance, the holder 905 can be a metal plate and component 902 is a magnet that pulls the plate in a neutral position.

Both FIGS. 9a and 9b thus illustrate transducers that utilize a change of a non-linear shape of a DFB fiber laser to capture or calculate a change in a physical measurand, such as temperature or pressure, for example. This non-linear shape can be a circular shape or an approximation of a circular shape that can be characterized, for instance, by a radius of the circle shape or approximate circular shape of the DFB fiber laser. The non-linear shape may also be a parabola or any other conic section that can be represented by one or more parameters. In accordance with an aspect of the present invention, a value of a parameter that determines a non-linear shape of a DFB fiber can be associated with a value of a measurand via a transducer that changes a fiber shape when the measurand changes in value.

These transducers can operate in a repeatable manner, so that a value of a measurand is changed into a measurable change of the DFB fiber (which can be measured through the beat note) in a repeatable manner. One can calibrate the transducer and a resulting shape parameter (such as a fiber radius) against the beat note in such a manner that a beat note can be directly associated with a value of a measurand, for instance by using a calibrated look-up table.

In addition to the bent DFB fiber laser 901, a straight DFB laser 903 is shown in FIG. 9b. This laser 903 will not be bent or put under strain or stress and thus can be used to measure changes to a different measurand, such as temperature. Since the DFB laser 903 is attached in such a way that pressure is not applied to it, any change in beat note is due solely to any temperature change. The bent DFB laser 901 experiences the effects both from temperature and pressure. Comparing the nature of beat frequency changes of the two DFBs, it is thus possible to differentiate temperature and pressure. This process is applied in one embodiment of the present invention to adjust for the temperature dependence of the bent DFB laser 901. In general, a number of measurands n may be measured by configuring n DFB lasers such that each has a different response to the influence of the measurands.

Also shown in FIG. 9b is detector 904 for detecting the beat frequencies of fiber lasers 901 and 903 and the change in the beat frequencies due to pressure, temperature or both measurands, as an example. In the event when two polarization modes of 901 (and also 903) becomes perfectly orthogonal at the receiver after travelling through the fiber that connects the laser to detector, in order to ensure that a beat note will be present at a detector 904 it may be necessary to employ polarization diversity detection. Such detection measures the power in two polarization projections, thus ensuring that if a first projection shows no beat note, a second one will. This is, because depending on the relative orientation of the two polarization states at the input of the polarizer, the output of one projection can be close to zero, so the beat not signal will be hard to detect. In yet another embodiment of the present invention, the detector 904 in FIG. 9b is accompanied by an optical spectrum measurement. Typical output spectra showing beat notes that are characteristic to the bend and straight DFB lasers are shown in FIG. 9b. In such a case, both the RF and optical spectrum measurements may be used to obtain the bend and temperature states (or the pressure and temperature states) of the transducer apparatus 900b.

In another preferred embodiment of the present invention, the fiber is a birefringent fiber throughout the entire system, including the section between the DFB lasers and the section that connects these to the WDM and the photodetector. In order to ensure a strong beat note at the detector such as detector 904, a polarizer oriented at 45 degrees to the two axes of the birefringent fiber is introduced in the pathway to the detector. In yet another embodiment of the present invention, there are many DFB fiber lasers, where the birefringence of each DFB is tailored to give an RF beat note at a different RF frequency. As is apparent from the above discussion of the polarization beat note, the fiber birefringence controls the RF offset. Thus, many DFB sensors on the same fiber may be read with the measurement of the RF spectrum of the combined laser outputs.

In one embodiment of the present invention the DFB bend sensor from which a beat frequency is determined as a function of a bending variable (such as a radius) is used as a pressure sensor in a well, such as a gas well or an oil well.

Figure 10:
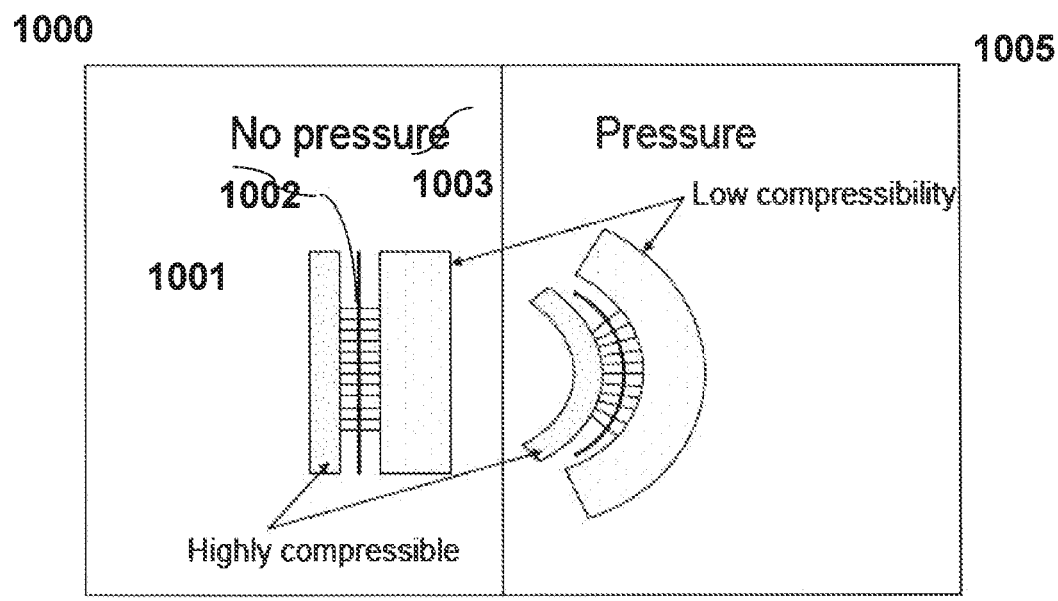
FIGS. 10-15 illustrate a fiber in accordance with one or more aspects of the present invention.

In yet another embodiment of the present invention, the grating of the DFB laser is embedded in a material with differential compressibility. Thus, when a change in pressure occurs, the embedding material deforms, thus bending the grating. FIG. 10 illustrates this embodiment in a cross-sectional diagram 1000 which shows a fiber having a grating 1002 in a straight configuration disposed between a highly compressible material 1001 and low compressible material 1003 under a normal condition, that is, placed in a known pressure environment, such as ambient pressure, for example. A change in this pressure is shown in diagram 1005. The configuration shown in FIG. 10 can be achieved, as one example, using dual coatings applied to one or more gratings within a length of fiber, where one coating is a highly compressible material and a second coating is a material chosen to have low compressibility. When applied to a bend sensitive grating, such a configuration can function as a fiber pressure sensor.

In accordance with an aspect of the present invention, FIG. 10 could be described as showing a fiber with a grating 1002, such as a DFB fiber, encapsulated at least on one part with a first coating 1001 and on a second part with a second coating 1003. These two coatings 1001 and 1003 have different overall deformation coefficients and, thus, deform differently respect to one another in response to a changing measurand, such as a temperature or a pressure. A coating may also deform because of a chemical reaction with a material in the environment. Each coating may deform differently in response to this reaction. Another aspect of this embodiment includes one coating deforming under the influence of a measurand while the other coating does not. As a further aspect of the present invention, a DFB fiber laser, or a grating with a laser material is embedded in an optical guide or a sensor that has a cross sectional shape that is substantially rectangular, such as a ribbon shape, or at least not circular. Such a ribbon shape enhances the effect of different coatings at different sides of the ribbon.

In another embodiment of the present invention, the coatings 1001 and 1003 are the same material but each has a different thickness with respect to the other. In yet a further embodiment of the present invention, either coating 1001, 1003 or both comprise a plurality of coatings, that is, more than one layer of a coating is applied to create a total coating on either one or both sides of the grating 1002. In yet a further embodiment of the present invention, the DFB fiber laser has only one coating, such as either coating 1001 or 1003, attached to one side of the DFB fiber laser.

Because of the difference in the coefficient of deformation of each of the coatings applied at different sides of the fiber or ribbon, the shape of the fiber or ribbon will experience a deformation, with the fiber or ribbon following the shape of the coating with the greatest amount of deformation, and resulting in a bending of the fiber or ribbon. This bending can, as explained above, be translated into a signal with a beat frequency that depends on the amount of bending of the fiber or the ribbon.

In accordance with yet a further embodiment of the present invention, a DFB fiber laser is attached to a surface that changes in shape due to a changing measurand. As an example, a DFB fiber laser can be attached to a surface of a flexible material, such as an elastic polymer, for example, a balloon. As the pressure changes on the inside of the balloon, the balloon expands or contracts, causing a change to the bend of the DFB fiber laser. Other surfaces of objects that change in shape (such as made from shape memory materials such as alloys and polymers) for instance due to temperature changes may also be used as carriers or transducers for bending parameter-based DFB sensors.

In yet a further embodiment of the present invention, a sensor in an initial position is already bent. An increase or decrease of the measurand changes the amount of bending in the sensor, which can be detected by the beat signal originating from the DFB fiber laser.

In yet another embodiment of the present invention, the DFB fiber is replaced by a fiber with a plurality of cores. In this embodiment, a DFB grating is inscribed in more than one core. A bend will then give rise to a change in the stress state in one or more of the cores. A measurement of the laser frequencies either optically or by the measurement of the RF beat notes will then give the bend state and can be used to ultimately compute a change in the measurand. The beat notes can arise from the DFB lasers in each core operating in multiple modes, or by using the response from each DFB laser to create the beat note.

In yet another embodiment of the present invention, an element with polarization dependent loss (PDL) is included in the path between the DFB fiber laser and the detector. The PDL can be large as in a polarizer, or smaller. It may also be bulk or distributed. It may also be placed close enough to the grating that its orientation may be adjusted during fabrication so that the orientation of this PDL is always misaligned with respect to the two polarization Eigenstates of the DFB. For example, the DFB may lase on linear 0 and 90 degrees, and the PDL element may be oriented at 45 degrees to ensure beating of the two modes. Alternatively, polarization diversity optics may be placed in front of the detector. For instance one may include a splitter followed by a 0 degree polarizer in one arm and a 45 degree polarizer in the other arm. These two RF signals are then added using, for example, a summing amplifier. Phase shifts in the RF or optical domain could be added to ensure an RF beat note regardless of the input state of polarization. Alternatively the detector could be replaced by a polarimetric optical head which measures the projection of the input signal onto multiple polarization states. These signals are added in a summing amplifier in the RF domain. Phase shifts in the RF or optical domain could be added to ensure an RF beat note regardless of the input state of polarization.

In another embodiment of the present invention the RF frequency is measured by phase locked loop (PLL) circuitry. The readout from the phase locked loop then gives the RF signal.

Figure 11:
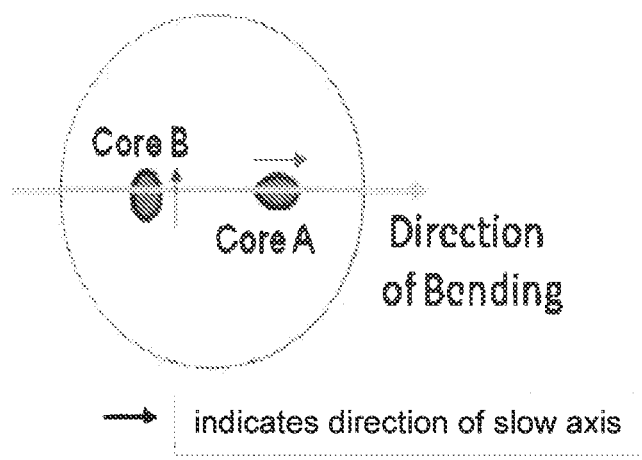

The requirement of two DFB lasers (a bent DFB laser and a straight DFB laser) to determine temperature and pressure can also be fulfilled by a properly engineered dual core DFB fiber laser, wherein two separate DFB fiber lasers are located within a single fiber. For example, by making DFB cavities in a dual core PM fiber with cores (Core A and Core B) having slow axes perpendicular or substantially perpendicular to each other as illustrated in FIG. 11, one obtains beat notes for the two DBF lasers that will follow the equations, $\Delta v_A = C_{0A} + C_{1A} \cdot T + C_{2A}/R^2$ and $\Delta v_B = C_{0B} + C_{1B} \cdot T - C_{2B}/R^2$. By measuring the beat notes of such a dual-core bent DFB laser, T (temperature) and R (bend radius) can be determined. Substantially perpendicular herein means that the angle between the two slow axes differs 10 degrees at most from 90 degrees.

Figure 12:
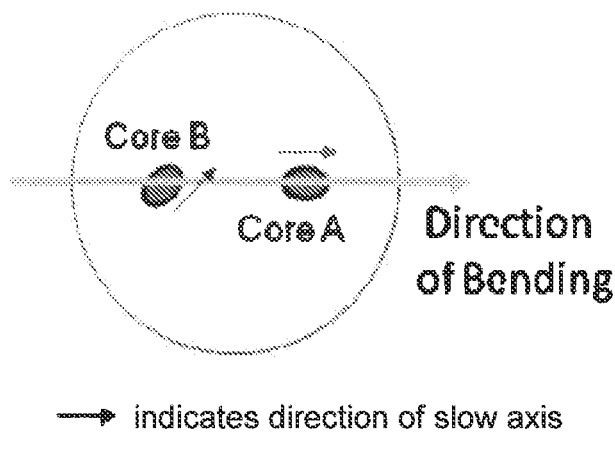

Alternatively, as illustrated in FIG. 12 the slow axis of one core can be made 45 degree or substantially 45 degrees with respect to the other core, so that, when the laser is bent in the direction shown, the beat frequency of the DFB laser in core B will not change. Substantially 45 degrees herein means that the angle does not differ more than 5 degrees from 45 degrees. The beat notes of each DBF laser corresponding to cores A and B, respectively can be written as $\Delta v_A = C_{0A} + C_{1A} \cdot T + C_{2A}/R^2$ and $\Delta v_B = C_{0B} + C_{1B} \cdot T$. Measurement of $\Delta v_A$ and $\Delta v_B$ will allow to determining T and R.

Figure 13:
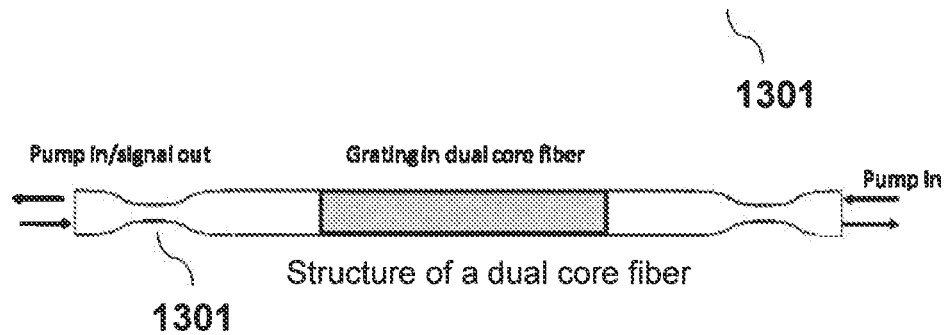

Further, the launching of pump light into the dual cores and extraction of the signal light from the cores can be done by tapering a short section of the fiber as shown at 1301 in the FIG. 13, so that light (pump and/or signal) can coupled from one core to the other. In FIG. 13, one or more sections of the dual core, located substantially away from the grating section (shown by gray region), are tapered, thereby bringing the two cores closer to one another. This tapering allows for a pump applied in either of the cores to split into two to excite both lasers. Also, a same taper, when designed appropriately, will allow both the pump signal and the laser output to mix at the tapered region 1301 and both be detectable in either of the two cores. Tapering opposite ends of the fiber allows for the pump to be applied from either end, as well as the laser output can be extracted from the other end. This allows light to be extracted from both DFB lasers using a single output port. A similar function may be performed using well-known fiber couplers, such as 3 dB fused fiber couplers.

In yet another embodiment of the present invention, the grating in each of cores A and B is written with slightly different center wavelengths respective to the other, such that the combined output can be separated using optical filters, and the RF beat note from each laser can be detected with ease.

Figure 14:
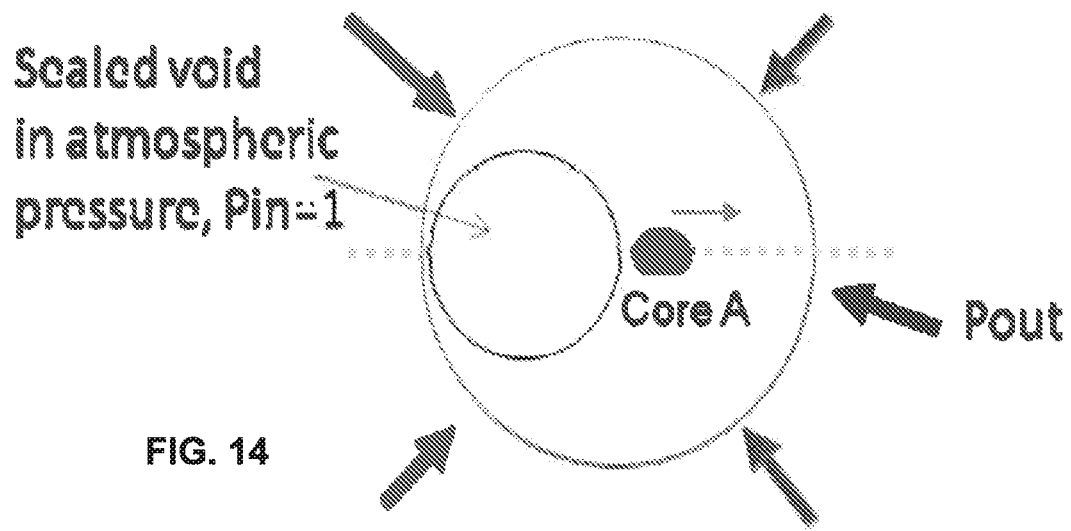

In another embodiment of the present invention, a fiber is provided with a hollow cavity or sealed void extending longitudinally along the fiber, which is located asymmetrically with respect to a core, such as Core A, as illustrated in FIG. 14. In the exemplary embodiment of FIG. 14, the pressure inside, $P_{in}$, the sealed void is at atmospheric level. When there is a pressure difference between the hollow cavity and the outside of fiber ($P_{out}$), the fiber will deform in asymmetrical manner with respect to the two polarization axes of the core and will tend to bend or introduce birefringence. Therefore, one will be able to measure the pressure difference experienced by the fiber directly without requiring any mechanical fixture.

Figure 15:
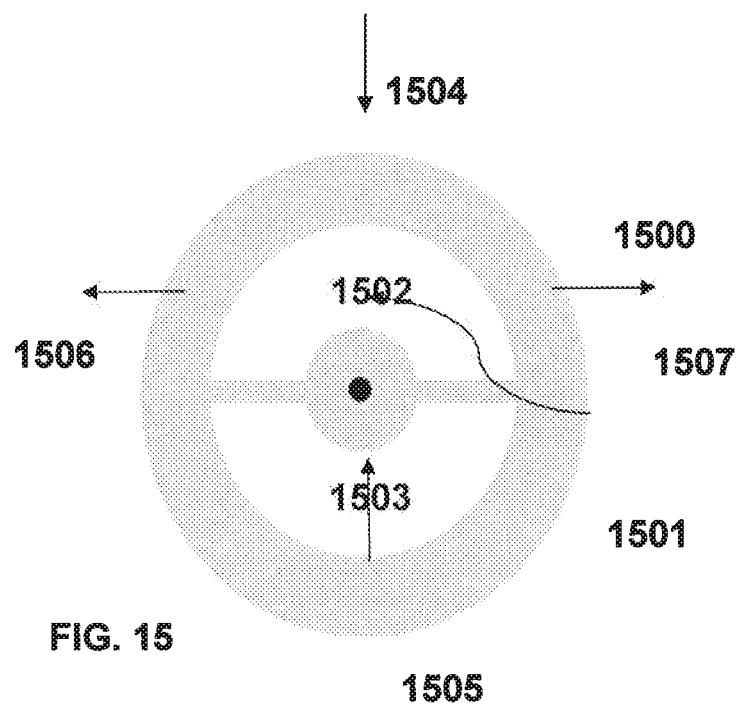

In yet another embodiment of the present invention, a fiber having a hollow structure on both sides of the core is used as a pressure sensor element. As shown in FIG. 15, a pressure sensor element contains a fiber 1500 having, at least, a DFB laser core 1501, and, at least, two cavities or voids 1502 and 1503, each having an internal pressure that is the same with respect to the other. Similar to FIG. 14, when the surrounding pressure of fiber 1500 changes with respect to the pressure inside the cavities 1502 and 1503, the strain on the fiber will be radially asymmetric, and cause a birefringence and beat note change, as illustrated in FIG. 15. For example, when the pressure is higher outside the deformation at 1504 and 1505, this differential will cause an outside deformation in direction 1506 and 1507, thereby causing a strain in core 1501, and thus a change in birefringence.

FIG. 10, FIG. 14, and FIG. 15 each show distributed laser fiber configurations that have cross-sectional anisotropic pressure properties that cause radially asymmetric strain of the fiber which cause the fiber to bend as a result of changing pressure. Bending, as was explained above, causes a birefringence change that can be measured as a change in a beat frequency. No fiber holders are thus required to force the fiber into a different bending state by changing an external pressure. However, at least one fiber holder may be used to keep the radially anisotropic pressure sensitive fiber in place.

Figure 16:
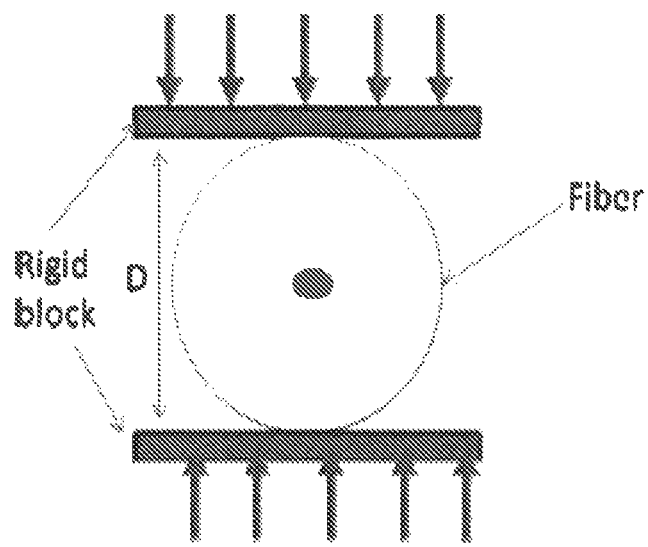
FIG. 16 illustrates a device in accordance with an aspect of the present invention.

The spring arrangement as illustrated in FIGS. 9a and 9b was described as sensitive to acoustic vibrations. Thus, when sound waves impinge on the device, the motions of the spring will cause the bent DFB fiber laser to vibrate. Note that though a spring can be used it is not necessary to have a spring. It is only necessary to have acoustic sensitivity, i.e., that acoustic vibrations are converted into a changing bend of the DFB laser. The motion of the DFB laser will then impose a frequency modulation on the DFB RF beat note. In another embodiment of the present invention, a heterodyne demodulation scheme demodulates this signal to produce a base band signal that reproduces the original sound wave. One such heterodyne scheme employs a phase locked loop. The voltage controlling the voltage controlled RF would then contain the sound signal. Thus, the bent DFB laser acts as an all-optical microphone with heterodyne detection. Instead of inducing a bend change in the fiber with a change in pressure, one can apply stress to the fiber in either the direction of slow and first axis as shown in FIG. 16. This induces a change in birefringence and create a beat note. Therefore, measurement of the beat note of a DFB laser made with such structure will allow for measurement of the pressure due to the applied stress, and temperature due to the birefringence change.

Figure 17:
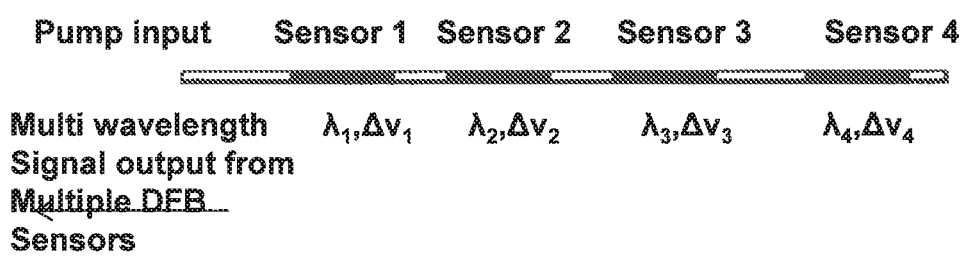
FIG. 17 illustrates a fiber in accordance with an aspect of the present invention.

In yet a further embodiment of the present invention a number of sensors are cascaded as an array as shown in FIG. 17. This can be pumped from one end by a common pump radiation, and light from each DFB sensor element (which preferably has different center wavelength, so that they do not interfere with each other) can be outputted from one end and interrogated to extract the information of beat notes of individual elements.

Figure 18:
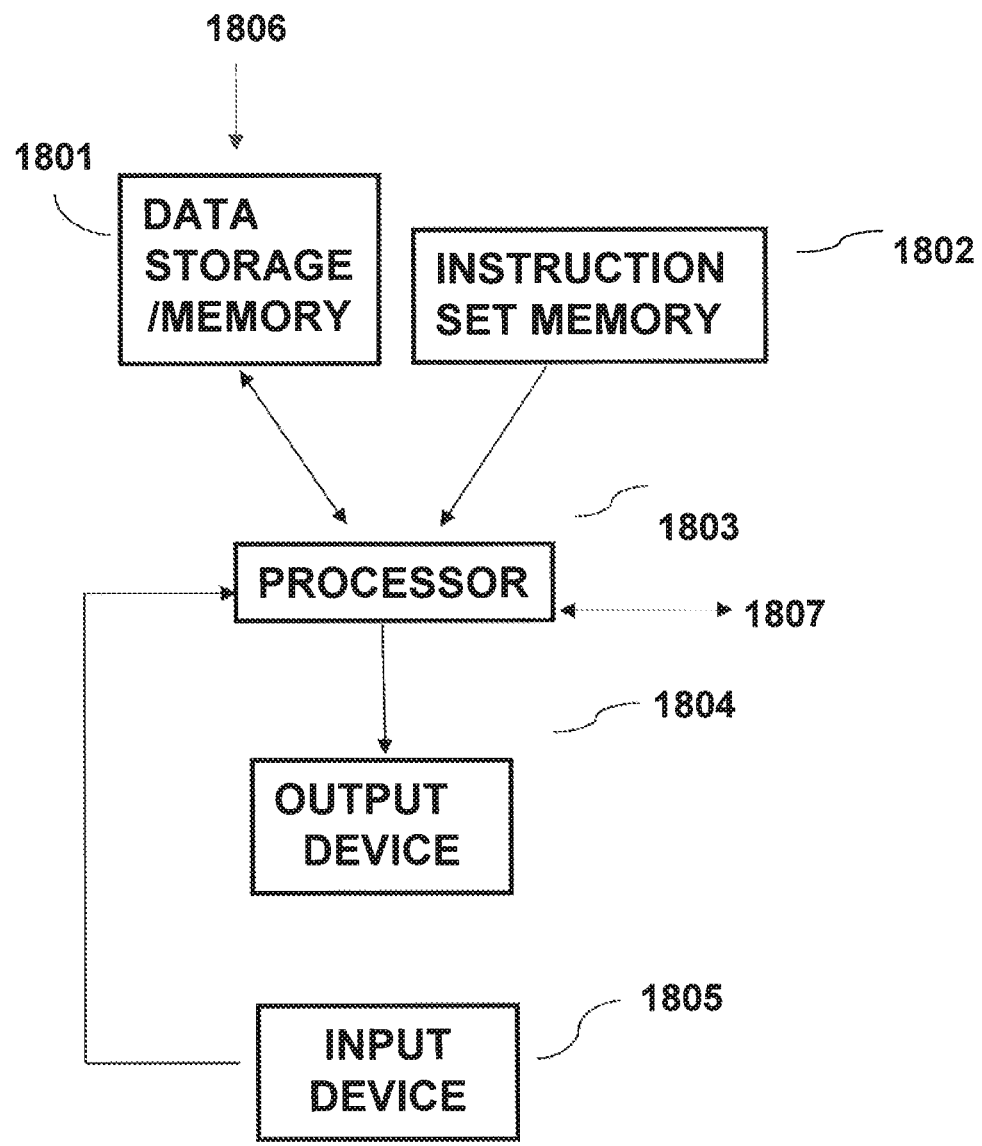
FIG. 18 illustrates a system in accordance with an aspect of the present invention.

According to an embodiment of the invention, signals such as those generated by the fiber DFB laser and the associated data can be processed by a system as shown in FIG. 18. The system is provided with data obtained from the fiber DFB laser and comprises a data or storage memory medium 1801, a set of executable instructions stored on a memory medium 1802, and a processor 1803. Data may be provided from multiple inputs, such as data 1806 received from the sensor. Data, for example, measurement data may be provided by an input device 1805, which, in one embodiment, is a phase locked loop (PPL) circuit. For example, such data may be provided on a continuous basis. A program comprising, at least, a set of instructions for executing methods of the present invention is stored on memory 1802 and is provided to the processor 1803, which executes the instructions of 1802 to process the data 1801. Data, such as representing a temperature, a radius or an acoustic signal or any other signal resulting from the processor can be outputted on an output device 1804, which may be, for example, a display or a loudspeaker to provide an acoustic signal. The processor may have a communication channel 1807 to receive other data from a communication device and to transmit data to an external device. The processor can be dedicated hardware. However, the processor 1803 can also be a CPU or any other computing device that can execute the instructions of 1802. Accordingly the system as illustrated in FIG. 18 provides a system for data processing resulting from a sensor and apparatus as provided herein and is enabled to execute the steps of the methods as provided herein as an aspect of the present invention.

Figure 19:
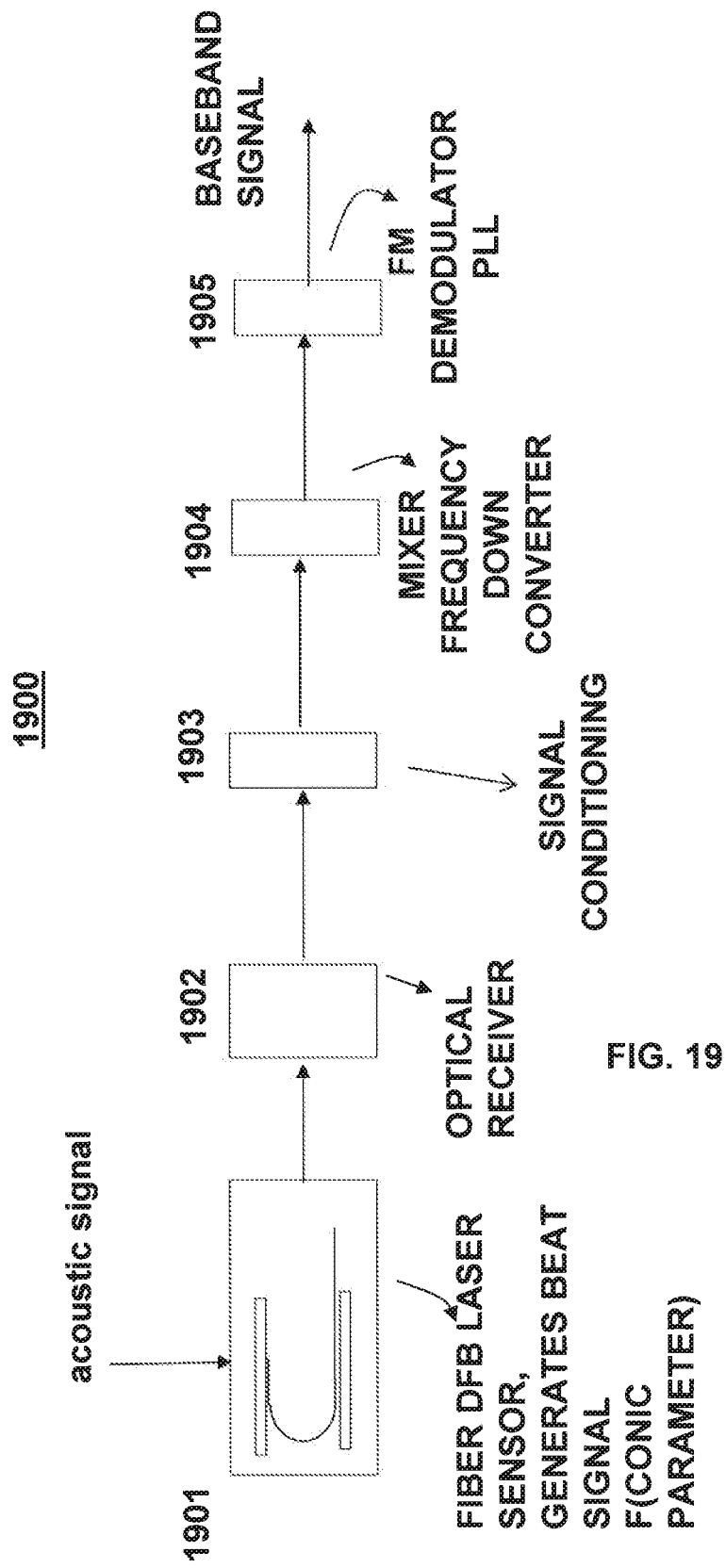
FIG. 19 shows an optical heterodyne microphone.

FIG. 19 illustrates an acoustical sensor, such as a microphone, in accordance with an aspect of the present invention. An acoustical/optical transducer 1901 is formed by a bent fiber DFB laser that is positioned similar to the DFB lasers as is illustrated in FIGS. 9a and 9b. The shape of the fiber in a neutral position in one embodiment of the present invention is already in a bent shape with a circular form. In yet another embodiment of the present invention, the shape of the bent fiber is one of a conic section and is at least partially shaped as a circle, ellipse, parabola or hyperbola. In yet another embodiment of the present invention, the shape of the bent fiber is in a smooth arc or curve that can be approximated by a conic section. A resulting beat note generated by the DFB laser having a particular smooth shape can be characterized by its present shape or shape parameters and a distortion or change to the present shape or shape parameters. Using a circular shape and the radius as its shape parameter is just one illustration of shape dependent birefringence in a fiber DFB laser.

Returning to FIG. 19, an acoustic signal is received on the transducer 1901. The acoustic signal causes a shape change of the fiber. While not shown in FIG. 19, it is assumed that the fiber DFB laser in 1901 is provided with a pump laser signal and has connectors to couple the pump laser into the fiber and decouple the generated laser light. The acoustic signal causes a shape change which may be a change in bend radius or other shape parameter, that causes an optical beat note to be generated from the lasing signals. Lasing signals are mixed to generate a beat note signal in an optical receiver or detector 1902 and to generate an electrical radio frequency (RF) signal. The generated electrical signal can be filtered and/or amplified or otherwise conditioned by a signal conditioner 1903. The RF signal can be mixed down in frequency by a heterodyne mixer 1904 and demodulated by a PLL demodulator 1905 to generate a demodulated signal which may be called a baseband signal.

The frequency of the beat signal varies in accordance with a change of the shape of the fiber DFB laser, which varies in accordance with a signal, such as an acoustic signal. Accordingly, the frequency of the beat signal varies in accordance with an acoustic signal and the generated beat signal represents a frequency modulated acoustic signal. In one embodiment of the present invention, the fiber has a circular shape with a radius smaller than 15 cm. In a further embodiment the fiber has a shape of a circular shape with a radius that is smaller than 10 cm. In a further embodiment, the fiber has a shape of a circular shape with a radius that is smaller than 5 cm.

For demodulation of the modulated signal, the beat signal may be provided to a heterodyne receiver or mixer 1904, which down converts the frequency modulated signal to a lower frequency band, for instance to a frequency band wherein a PLL or FM demodulator operates.

The electrical signal is then provided to a FM demodulator 1905. This can be implemented as a phase-locked-loop (PLL) circuit. The output of the FM demodulator 1905 is proportional to the beat note frequency, i.e. a measure of external perturbations.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims appended hereto.

The invention claimed is:

1. A sensor to sense a measurand, the sensor comprising:
   a fiber comprising a fiber core;
   a fiber laser cavity formed by a single fiber grating in the fiber core, the fiber laser cavity having at least two modes along at least part of its length, the fiber laser cavity including a first section that is bent in a non-linear shape, the non-linear shape having a radius of curvature (R), a change in the measurand causing a shift in a RF beat note ($\Delta v$), the $\Delta v$ being a function of $(1/R)^2$; and
   at least one pump laser connected to the fiber laser cavity.

2. The sensor of claim 1, further comprising a structure connected to the fiber that converts a change in the measurand into a change of the non-linear shape of the first section of the fiber laser cavity.

3. The sensor of claim 1, the sensor comprising a RF detector connected to the fiber laser cavity.

4. The sensor of claim 1, wherein the single fiber grating is a distributed feedback laser.

5. The sensor of claim 1, wherein the fiber laser cavity has a fiber cross-section with anisotropic pressure properties that cause radially asymmetric strain of the fiber which cause the fiber to bend by itself as a result of changing pressure or vibrations.

6. The sensor of claim 4, further comprising an optical detector connected to the distributed feedback laser.

7. The sensor of claim 1, wherein the fiber laser cavity has a slow axis and a fast axis of birefringence along at least part of its length.

8. The sensor of claim 1, wherein the measurand is a pressure or a temperature or a vibration or a chemical reaction.

9. The sensor of claim 6, further comprising a frequency demodulator connected to the optical detector.

10. The sensor of claim 1, wherein the sensor is part of an optical heterodyne microphone.

11. A method of sensing a measurand with a sensor, the method comprising:
    exciting a fiber laser cavity with a pump laser; and
    exposing the sensor to a perturbation, the sensor comprising a fiber, the fiber comprising a fiber core, the sensor further comprising a fiber laser cavity formed by a single fiber grating in the fiber core, the fiber laser cavity having at least two modes along at least part of its length, the fiber laser cavity including a first section that is bent in a non-linear shape, the non-linear shape having a radius of curvature (R), a change in the measurand causing a shift in a RF beat note ($\Delta v$), the $\Delta v$ being a function of $(1/R)^2$, the sensor further comprising a pump laser connected to the fiber laser cavity.

12. The method of claim 11, wherein the perturbation is applied to a structure connected to the sensor.

13. The method of claim 11, comprising detecting a RF beat note generated by the perturbation with a RF detector connected to the fiber laser cavity.

14. The method of claim 11, wherein the fiber laser cavity has a fiber cross-section with anisotropic pressure properties that cause radially asymmetric strain of the fiber which cause the fiber to bend by itself as a result of changing pressure or vibrations.

15. The method of claim 11, wherein the fiber laser cavity has a slow axis and a fast axis of birefringence along at least part of its length.

16. The method of claim 11, wherein the perturbation is a pressure or a temperature or a vibration or a chemical reaction.

17. The method of claim 11, wherein a frequency demodulator demodulates a signal from the fiber laser cavity.

18. The method of claim 11, wherein the sensor is part of an optical heterodyne microphone.

19. A sensor to sense a measurand, the sensor comprising:
    a fiber having a radius of curvature (R);
    a first core located in the fiber, the first core supporting a first distinct mode, the first distinct mode having a first propagation constant, the first distinct mode being characterized by a first beat note;
    a first distributed feedback laser in the first core, the first distributed feedback laser being subject to a perturbation, the perturbation causing a first shift in the first propagation constant, the first shift causing a first change in the first beat note, the first change being a function of $(1/R)^2$;
    a second core located in the fiber, the second core supporting a second distinct mode, the second distinct mode having a second propagation constant, the second propagation constant being different from the first propagation constant, the second distinct mode being characterized by a second beat note, the second beat note being different from the first beat note,
    a second distributed feedback laser in the second core, the second distributed feedback laser being subject to the perturbation, the perturbation causing a second shift in the second propagation constant, the second shift causing a second change in the second beat note; and
    a RF detector connected to the fiber, the RF detector for detecting the first beat note, the RF detector further for detecting the second beat note.

20. The sensor of claim 19, further comprising one or more additional distributed feedback lasers located in the fiber.

* * * * *